(12) United States Patent
Huang

(10) Patent No.: US 11,072,101 B2
(45) Date of Patent: Jul. 27, 2021

(54) EARTIP, MOLD DEVICE FOR MANUFACTURING THE EARTIP, AND METHOD OF MANUFACTURING THE EARTIP

(71) Applicant: REXTEC INTERNATIONAL LIMITED, Taipei (TW)

(72) Inventor: Cheng-Houng Huang, Taipei (TW)

(73) Assignee: REXTEC INTERNATIONAL LIMITED, Taipei (TW)

( * ) Notice: Subject to any disclaimer, the term of this patent is extended or adjusted under 35 U.S.C. 154(b) by 441 days.

(21) Appl. No.: 15/496,597

(22) Filed: Apr. 25, 2017

(65) Prior Publication Data
US 2018/0071966 A1 Mar. 15, 2018

(30) Foreign Application Priority Data
Sep. 9, 2016 (TW) .................................. 105129311

(51) Int. Cl.
| | |
|---|---|
| H04R 1/10 | (2006.01) |
| A61F 11/08 | (2006.01) |
| B29C 45/14 | (2006.01) |
| H04R 31/00 | (2006.01) |
| B29C 43/02 | (2006.01) |
| G10K 11/18 | (2006.01) |
| A61F 11/00 | (2006.01) |

(Continued)

(52) U.S. Cl.
CPC ............ *B29C 45/14* (2013.01); *B29C 43/027* (2013.01); *G10K 11/18* (2013.01); *H04R 1/1091* (2013.01); *H04R 31/00* (2013.01); *A61F 11/008* (2013.01); *A61F 2240/001* (2013.01); *B29C 33/48* (2013.01); *B29C 45/02* (2013.01); *B29L 2031/3431* (2013.01); *H04R 1/1016* (2013.01)

(58) Field of Classification Search
CPC ........ A61F 11/008; A61F 11/06; A61F 11/08; A61F 2011/085; H04R 25/652; H04R 25/656; H04R 1/10; H04R 1/1016; H04R 1/1091
See application file for complete search history.

(56) References Cited

U.S. PATENT DOCUMENTS 2,489,277 A * 11/1949 Faralla ................. H04R 1/1016
181/22
5,113,967 A * 5/1992 Killion .................... A61F 11/08
181/132

(Continued)

*Primary Examiner* — Edgardo San Martin
(74) *Attorney, Agent, or Firm* — Rabin & Berdo, P.C.

(57) ABSTRACT

An eartip, mold device for manufacturing the eartip, and method of manufacturing the eartip are introduced, characterized by forming an upper bevel-portion with upper and lower molds of a first mold unit, placing the upper bevel-portion in an upper bevel receiving cavity of a second mold unit, forming a lower bevel-portion with a lower bevel cavity, and joining the upper and lower bevel-portions to form an eartip. The top of the lower hollow-cored guiding tube extends to form a buffer portion which connects and communicates with the upper hollow-cored guiding tube. The upper and lower bevel-portions are made of silicone of different rigidity. The upper bevel-portion thus made is soft enough to reach a user's ear canal deeply. The lower bevel-portion thus made is rigid enough to close the ear canal. An annular buffer cavity is inwardly, concavely formed at the bottom of the lower bevel cavity.

11 Claims, 16 Drawing Sheets

(51) Int. Cl.
*B29C 33/48* (2006.01)
*B29C 45/02* (2006.01)
*B29L 31/34* (2006.01)

(56) References Cited

U.S. PATENT DOCUMENTS

| | | | | |
|---|---|---|---|---|
| 6,148,821 | A * | 11/2000 | Falco | A61F 11/08 128/864 |
| 6,258,043 | B1 * | 7/2001 | Raviv | A61B 5/12 600/559 |
| 6,264,870 | B1 * | 7/2001 | Håkansson | A61F 11/08 264/222 |
| 6,286,622 | B1 * | 9/2001 | Tiemann | A61F 11/08 128/864 |
| 6,568,394 | B2 * | 5/2003 | Falco | A61F 11/08 128/864 |
| 6,695,093 | B1 * | 2/2004 | Falco | A61F 11/08 181/130 |
| 6,931,142 | B2 * | 8/2005 | Fushimi | H04R 1/1016 181/130 |
| 7,107,993 | B2 * | 9/2006 | Magidson | A61F 11/08 128/857 |
| 7,305,992 | B2 * | 12/2007 | Fleming | A61F 11/08 128/864 |
| 7,681,577 | B2 * | 3/2010 | Blanchard | A61F 11/08 128/846 |
| 8,189,846 | B2 * | 5/2012 | Tiscareno | H04R 1/1016 381/322 |
| 8,201,561 | B2 * | 6/2012 | Blanchard | A61F 11/08 128/846 |
| 8,348,011 | B1 * | 1/2013 | Huang | H04R 25/656 181/130 |
| 2015/0328052 | A1 * | 11/2015 | Kalden | A61F 11/08 128/867 |
| 2016/0022498 | A1 * | 1/2016 | Dittrich | A61F 11/08 128/864 |
| 2020/0314519 | A1 * | 10/2020 | Hatfield | H04R 1/1016 |

\* cited by examiner

EARTIP, MOLD DEVICE FOR MANUFACTURING THE EARTIP, AND METHOD OF MANUFACTURING THE EARTIP

CROSS-REFERENCE TO RELATED APPLICATION

This non-provisional application claims priority under 35 U.S.C. § 119(a) on Patent Application No(s). 105129311 filed in Taiwan, R.O.C. on Sep. 9, 2016, the entire contents of which are hereby incorporated by reference.

FIELD OF THE INVENTION

The present invention relates to eartips, mold devices for manufacturing the eartips, and methods of manufacturing the eartips and, more particularly, to an eartip, mold device for manufacturing the eartip, and method of manufacturing the eartip, characterized by forming a soft upper bevel portion from a first mold unit, and then placing the upper bevel portion in a second mold unit to form a rigid lower bevel portion.

BACKGROUND OF THE INVENTION

A conventional eartip essentially comprises a hollow-cored pipe with one end and an output end. The one end extends to form a casing. The output end is formed from a buffer whereby the casing becomes bendable and thus easy to insert into a user's ear canal. However, the eartip is incapable of reaching the ear canal deeply. Another conventional eartip discloses a hollow-cored pipe with a top end extending to form an upper bevel portion and a middle end extending to form a lower bevel portion. A buffer is disposed at the top end of the lower bevel portion such that the upper bevel portion is bendable. Although the upper bevel portion can reach the ear canal deeply and thus is unlikely to be disconnected therefrom, it is made of a material soft enough to render it disconnectable. If it is made of a rigid material, it may press against the ear canal and thus cause discomfort.

Conventional mold devices for manufacturing eartips and conventional methods of manufacturing the eartips are not effective in producing any eartip whose upper bevel portion and lower bevel portion differ in rigidity. The eartips produced by the conventional mold devices for manufacturing eartips and conventional methods of manufacturing the eartips have a drawback: each mold device is dedicated to a unique upper bevel portion and lower bevel portion, thereby rendering the production process inflexible and pricey.

In view of the aforesaid drawbacks of the prior art, it is important to make an eartip comfortable and unlikely to detach when placed in an ear canal, so as to ensure satisfactory hearing quality. Hence, the inventor of the present invention conducted extensive researches and experiments according to the inventor's years of experience in the related industry, and finally developed an eartip, mold device for manufacturing the eartip, and method of manufacturing the eartip, as disclosed in the present invention to achieve advantages as follows: a sound guide pipe is made with two molds segmentally and of different materials to bring acoustic variations.

SUMMARY OF THE INVENTION

In view of the aforesaid drawbacks of the prior art, it is an objective of the present invention to manufacture an eartip by forming an upper bevel portion from silicone of a rigidity of around 30±5, forming a lower bevel portion from silicone of a rigidity of around 40±5, and allowing the top end of the lower bevel portion to extend and thus form a buffer portion with an annular groove. The upper bevel portion thus made is soft enough to reach the ear canal deeply. The lower bevel portion thus made is rigid enough to close the ear canal. The buffer portion with a rigidity of around 40±5 is formed on top of the lower bevel portion to enable the upper bevel portion to bend when reaching the ear canal deeply, whereas the buffer portion is of an appropriate rigidity and thus does not bend readily, thereby allowing the upper bevel portion to reach the ear canal deeply.

Another objective of the present invention is to provide a mold device for manufacturing an eartip. The mold device comprises: a first mold unit comprising an upper mold and a lower mold, with an upper bevel cavity disposed between the upper mold and the lower mold, the upper mold being a protruding portion, the protruding portion being surrounded by an upper mold groove, the lower mold being provided centrally with a hemispherical recess, which the upper mold and the lower mold are stacked to form the upper bevel cavity; and a second mold unit comprising a first mold, a second mold, a third mold, a fourth mold and a fifth mold which are stacked in sequence to form the second mold unit, the first and second molds forming an upper bevel receiving cavity for receiving the upper bevel portion, the second, third, and fourth molds forming a lower bevel cavity, wherein the upper bevel receiving cavity and the lower bevel cavity are in communication with each other to form a pad cavity. The upper bevel portion and the lower bevel portion are made of silicone of different rigidity. The upper bevel portion comes in different sizes and still matches the lower bevel portion which is restricted to a specific size; hence, the upper bevel portion is effective in manufacturing eartips of different sizes, rendering the eartip manufacturing process flexible, and dispensing with the need for multiple molds.

Yet another objective of the present invention is to provide a method of manufacturing an eartip. The method comprises steps as follows:

step 1: placing an upper bevel portion raw material between an upper mold and a lower mold of a first mold unit;

step 2: forming an upper bevel portion from the upper bevel portion raw material by squeezing the upper mold and the lower mold of the first mold unit;

step 3: releasing the first mold unit by separating the upper mold and the lower mold of the first mold unit;

step 4: removing the upper bevel portion otherwise attached to one of the upper mold and the lower mold;

step 5: placing the upper bevel portion in the upper bevel receiving cavity between a first mold and a second mold of a second mold unit;

step 6: putting together the second mold, the third mold, and the fourth mold to form a lower bevel cavity and form at a bottom of the lower bevel cavity an annular buffer cavity which curves inward;

step 7: placing a lower bevel portion raw material in a raw material storage chamber of the fourth mold of the second mold unit;

step 8: fitting the fifth mold inside the fourth mold so that not only is the lower bevel portion raw material introduced into the lower bevel cavity to therefore form a lower bevel portion, but the upper bevel portion and the lower bevel portion also join each other to form an eartip; and step 9: performing mold release by separating the first mold, the third mold, and the fourth mold in a reverse order and then removing the eartip from the second mold.

Therefore, the method of manufacturing an eartip essentially entails forming an upper bevel portion of a low rigidity in a first mold unit, and then placing the upper bevel portion on a second mold unit to form a lower bevel portion of a high rigidity, wherein a buffer portion of a rigidity of 40±5 is disposed on the lower bevel portion so that the process of forming the lower bevel portion does not interfere with the upper bevel portion, thereby enhancing the quality of the eartip manufactured.

DETAILED DESCRIPTION OF THE PREFERRED EMBODIMENTS

To enable persons skilled in the art to gain insight into the technical solutions claimed by the present invention and achievable advantages, the present invention is hereunder illustrated by preferred embodiments, depicted with diagrams and described below in length. The present invention provides an eartip, a mold device for manufacturing the eartip, and the method of manufacturing the eartip.

Figure 1:
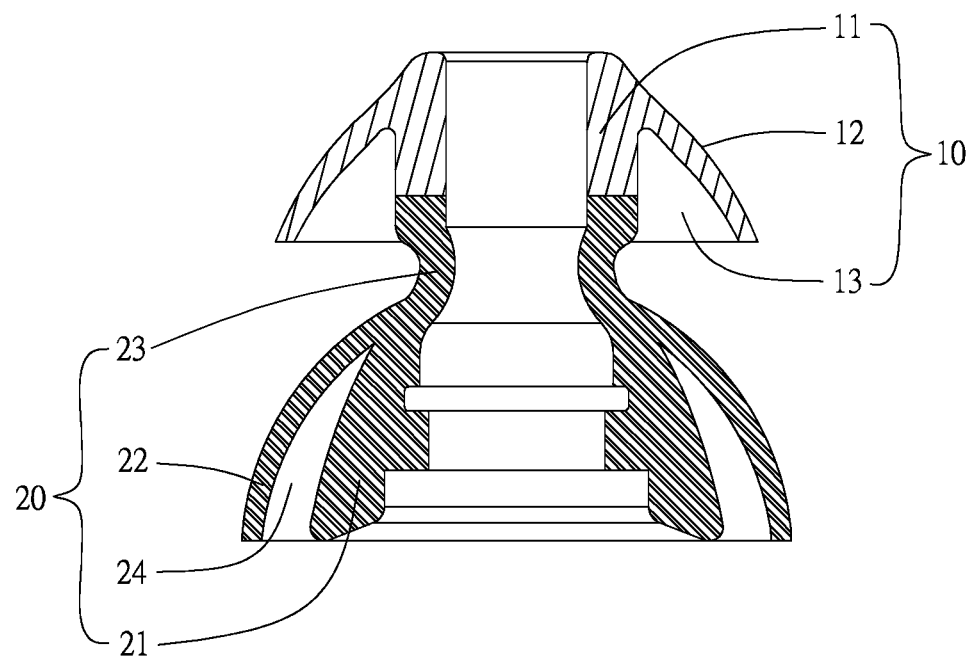
FIG. 1 is a schematic view of an eartip of the present invention.

Referring to FIG. 1, there is shown a schematic view of an eartip of the present invention. As shown in the diagram, the eartip comprises an upper bevel portion 10 and a lower bevel portion 20.

The upper bevel portion 10 is made of a silicone-containing material of a rigidity of 30±5 and comprises an upper hollow-cored guiding tube 11 and an upper bevel 12 which surrounds the top end of the upper hollow-cored guiding tube 11. A space 13 is disposed between the upper bevel 12 and the upper hollow-cored guiding tube 11.

Likewise, the lower bevel portion 20 is made of a silicone-containing material of a rigidity slightly higher than the upper bevel portion 10, that is, 40±5, and comprises a lower hollow-cored guiding tube 21 and a lower bevel 22 which surrounds the top end of the lower hollow-cored guiding tube 21. The top end of the lower hollow-cored guiding tube 21 extends to form a buffer portion 23 which has an annular groove. The buffer portion 23 connects and communicates with the upper hollow-cored guiding tube 11. A lower bevel space 24 is disposed between the lower bevel 22 and the lower hollow-cored guiding tube 21. The diameter of the bottom rim of the upper bevel 12 is less than the diameter of the bottom rim of the lower bevel 22.

Figure 2:
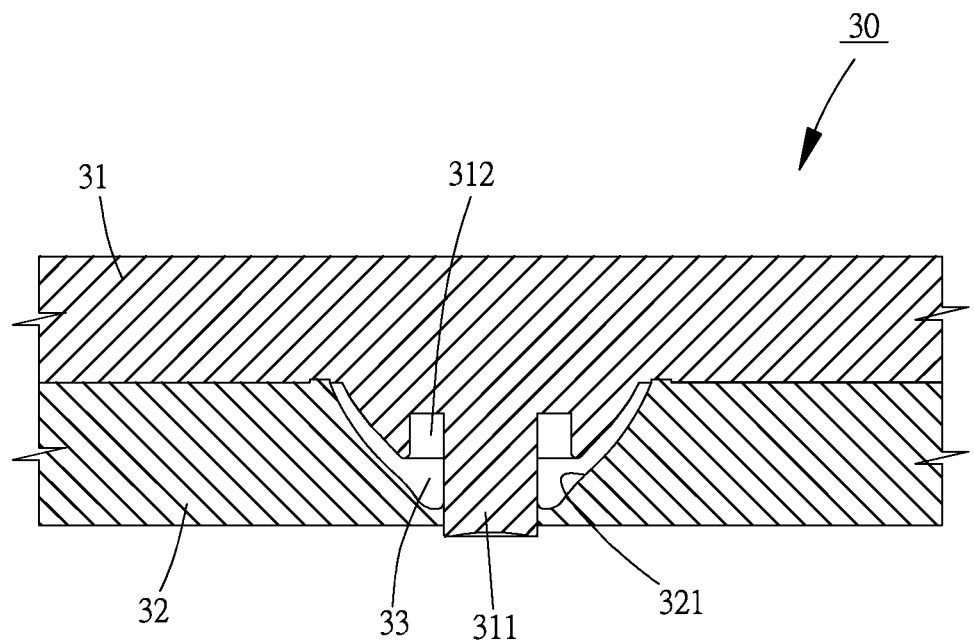
FIG. 2 is a cross-sectional view of a first mold unit for use in manufacturing the eartip of the present invention.
Figure 3:
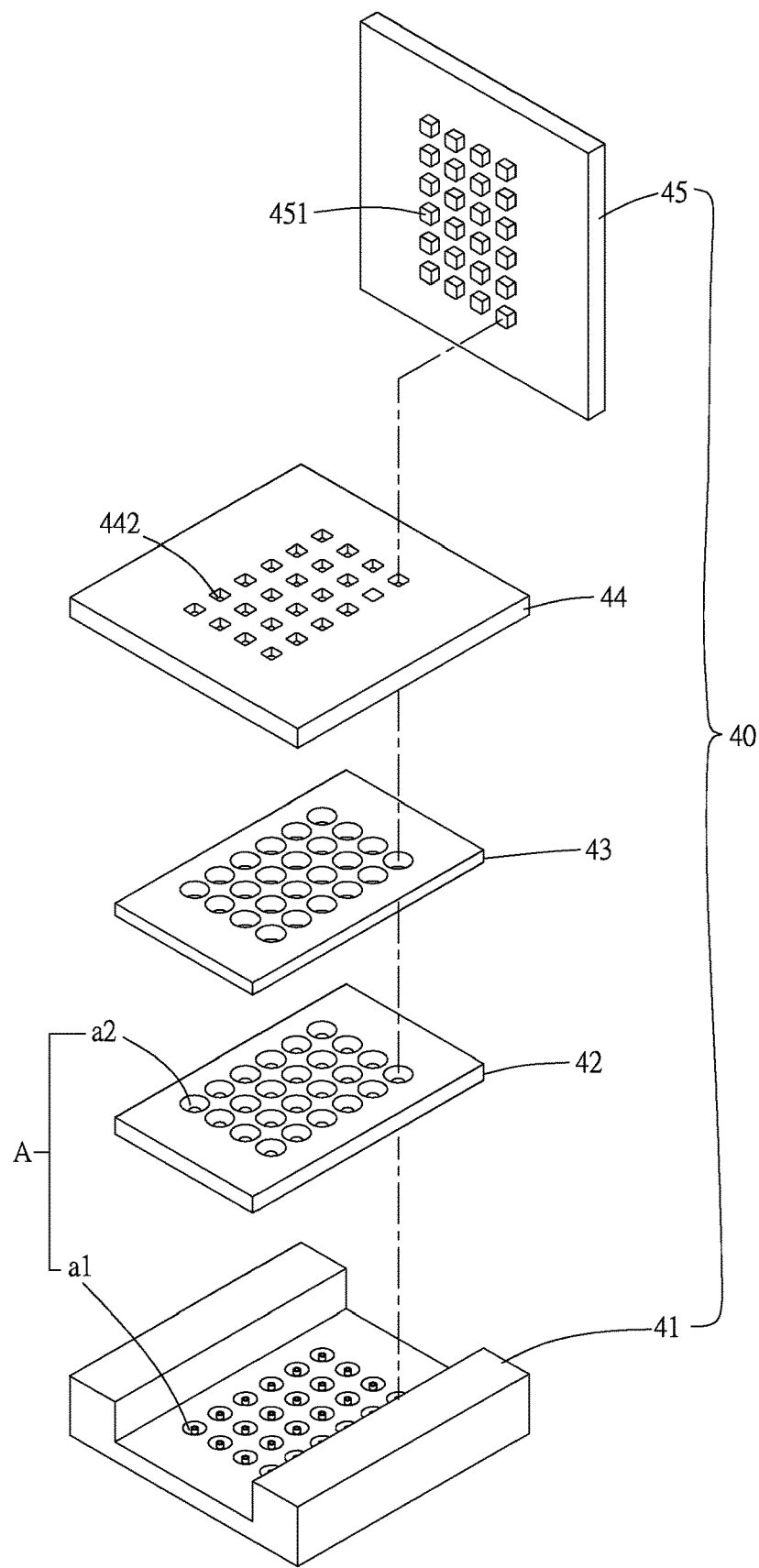
FIG. 3 is an exploded view of a second mold unit for use in manufacturing the eartip of the present invention.
Figure 4:
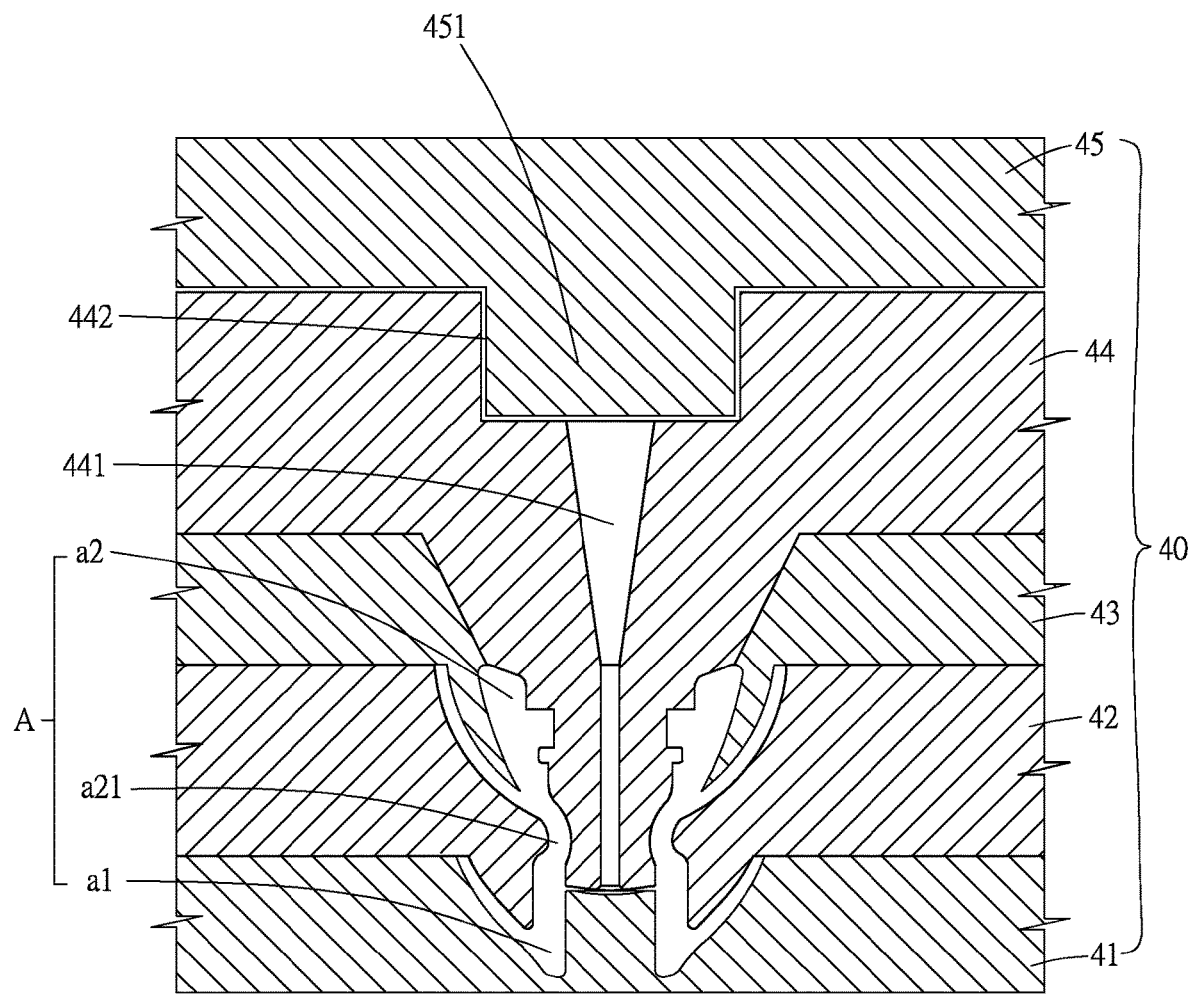
FIG. 4 is a cross-sectional view of the second mold unit for use in manufacturing the eartip of the present invention.

Referring to FIGS. 2-4, a first mold unit 30 for use in manufacturing the eartip of the present invention comprises an upper mold 31 and a lower mold 32. An upper bevel cavity 33 is formed between the upper mold 31 and the lower mold 32. A protruding portion 311 is disposed centrally at the upper mold 31 and surrounded by an upper mold groove 312. A hemispherical recess 321 is disposed centrally at the lower mold 32 and adapted to form the upper bevel portion 10 shown in FIG. 1. Referring to FIGS. 3, 4, there are shown an exploded view and a cross-sectional view of a second mold unit 40 for use in manufacturing the eartip of the present invention, respectively. As shown in FIGS. 3, 4, the second mold unit 40 comprises a first mold 41, a second mold 42, a third mold 43, a fourth mold 44 and a fifth mold 45. An upper bevel receiving cavity a1 is formed between the first mold 41 and the second mold 42 and adapted to receive the upper bevel portion 10. A lower bevel cavity a2 is formed between the second mold 42, the third mold 43, and the fourth mold 44. An annular buffer cavity a21 is inwardly, concavely formed at the bottom end of the lower bevel cavity a2. The upper bevel receiving cavity a1 and the lower bevel cavity a2 are in communication with each other to form a pad cavity A. The fourth mold 44 has a protruding hollow-cored raw material guiding pipe 441 and a raw material storage chamber 442. The fifth mold 45 has a protruding portion 451 and thus fits inside the raw material storage chamber 442; a raw material can be introduced from the raw material storage chamber 442 into the lower bevel cavity a2 through the hollow-cored raw material guiding pipe 441 to form the lower bevel portion 20 shown in FIG. 1 so that the upper bevel portion 10 and the lower bevel portion 20 join each other to form the eartip.

Figure 5:
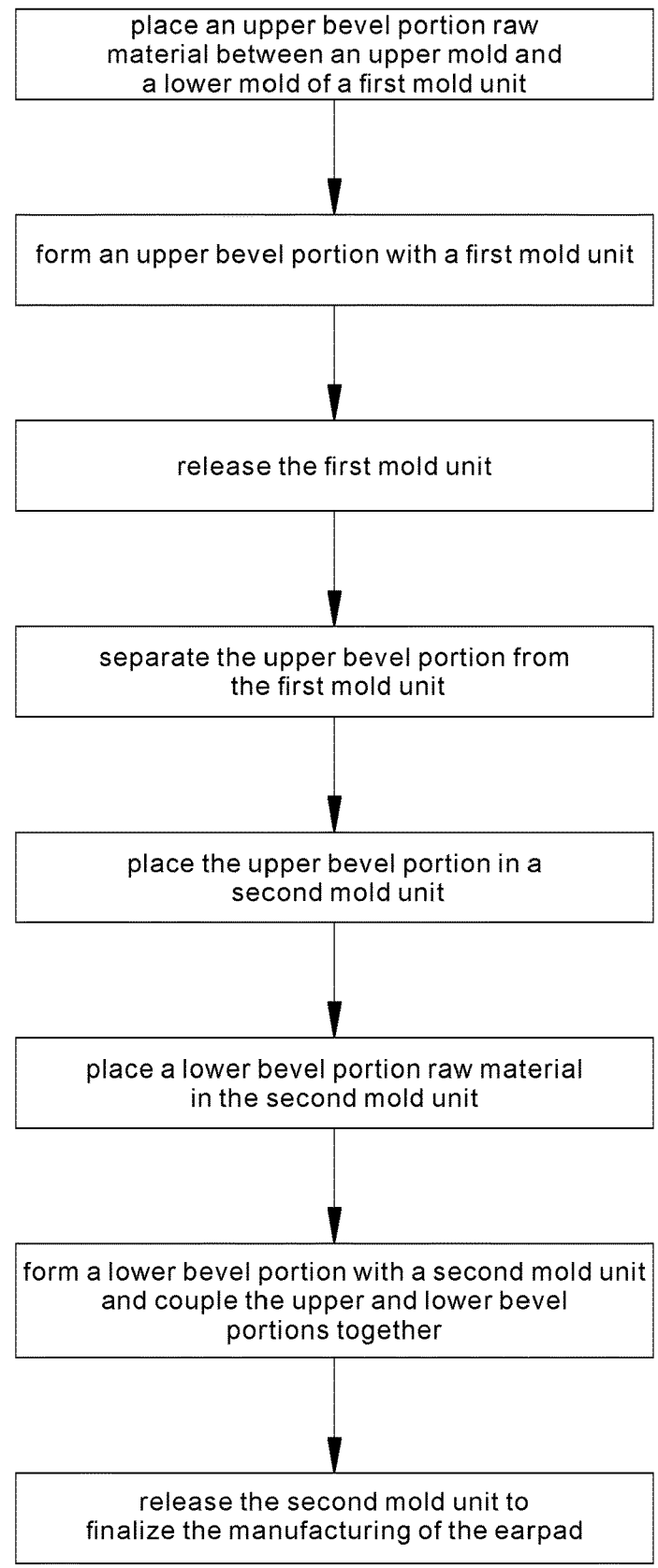
FIG. 5 is a schematic view of the process flow of a method of manufacturing an eartip according to the present invention.
Figure 6A:
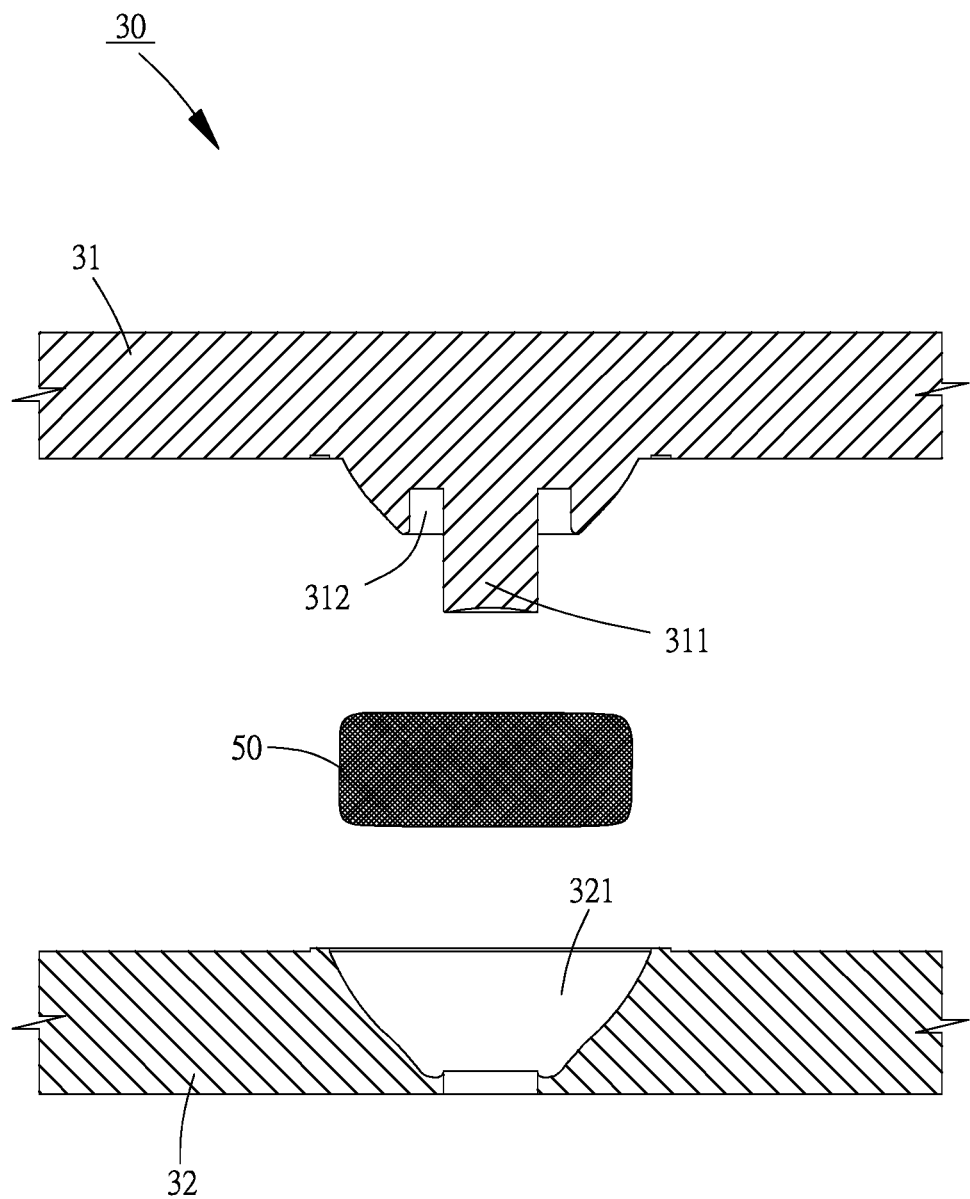
FIGS. 6A-6D are schematic views of how the first mold unit works in manufacturing the eartip according to the present invention.
Figure 6B:
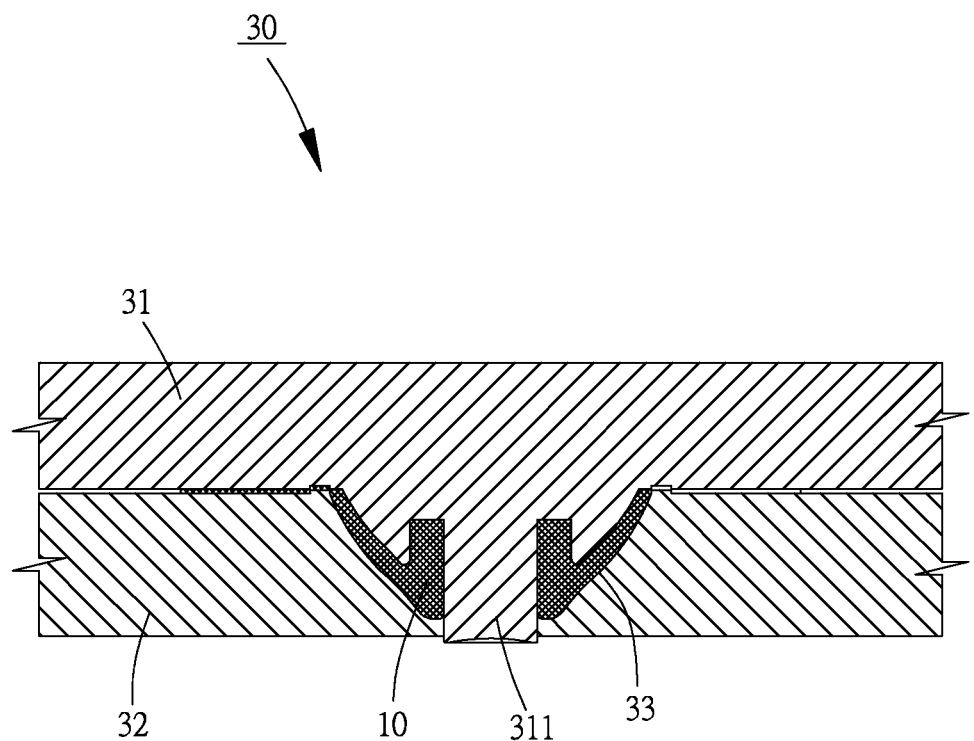
Figure 6C:
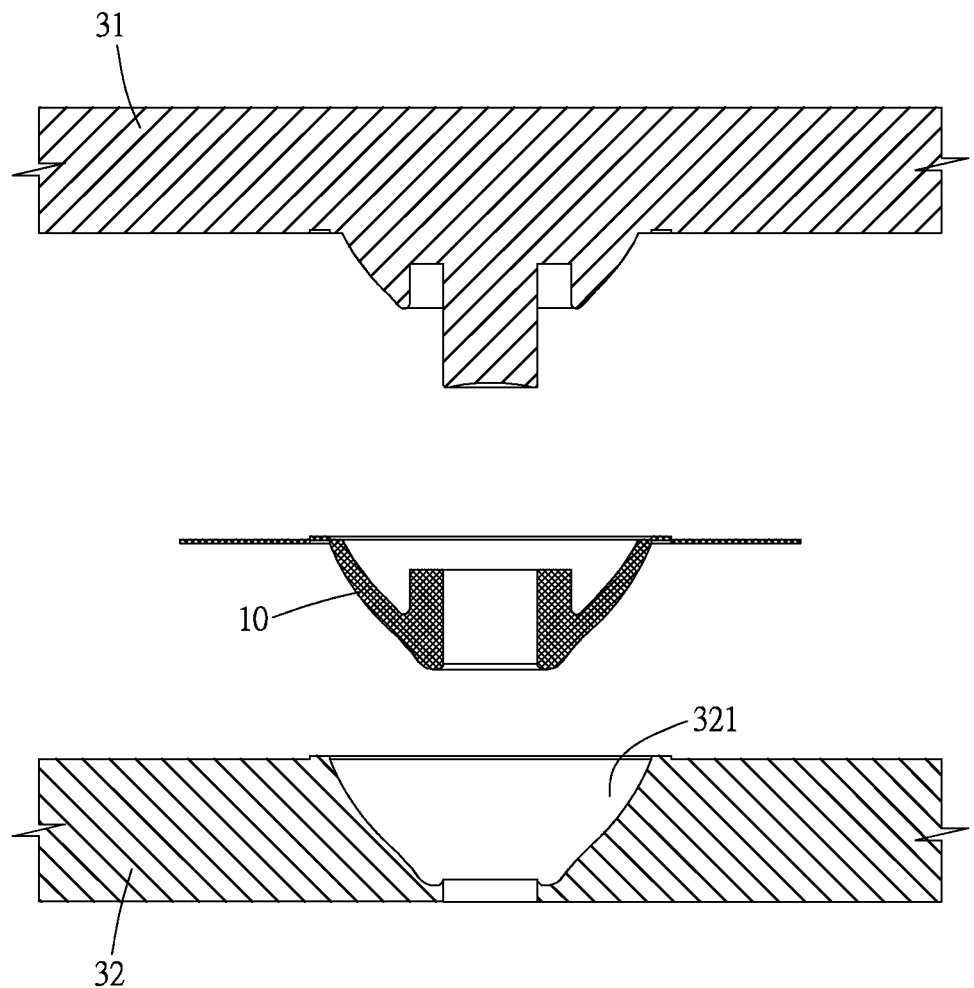
Figure 6D:
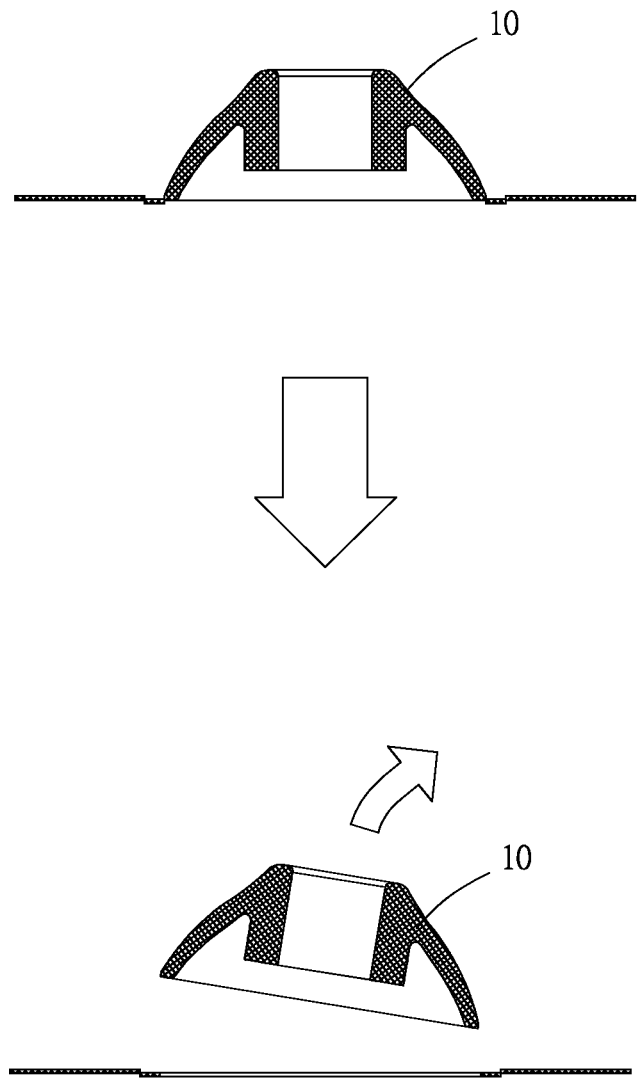
Figure 7A:
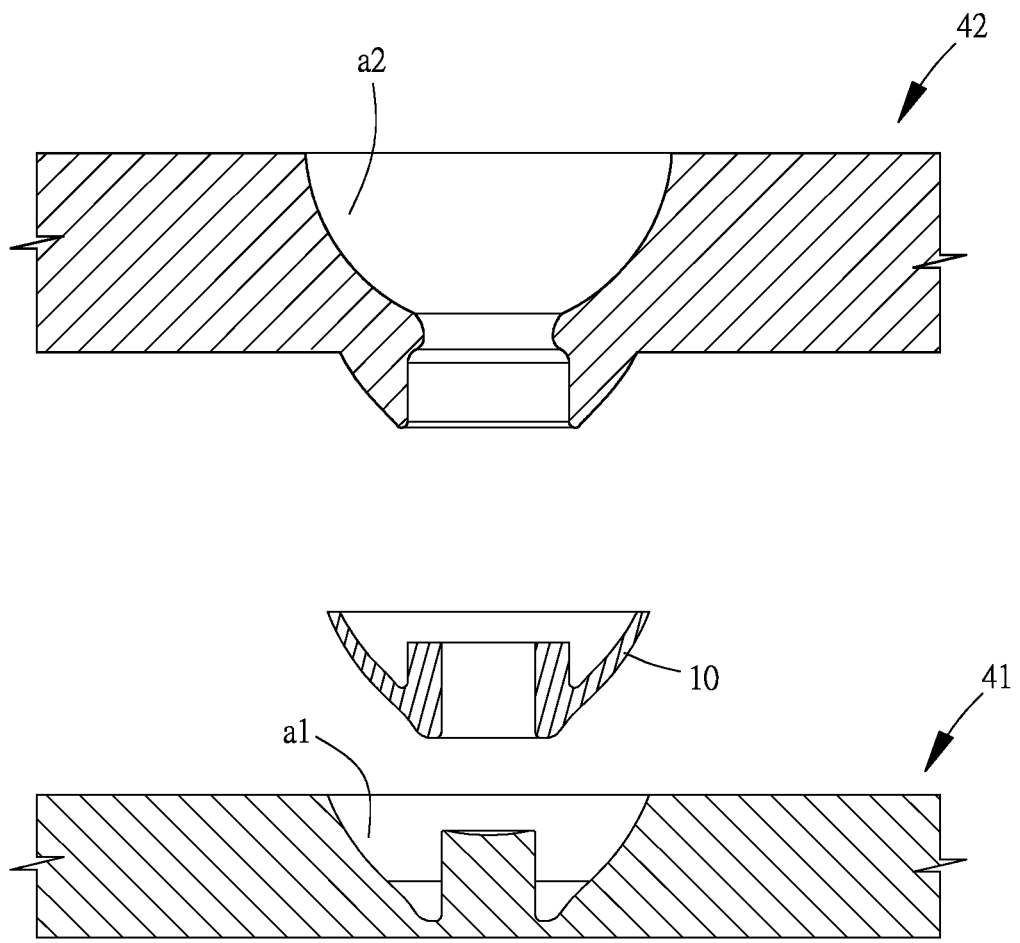
FIGS. 7A-7F are schematic views of how the second mold unit works in manufacturing the eartip according to the present invention.
Figure 7B:
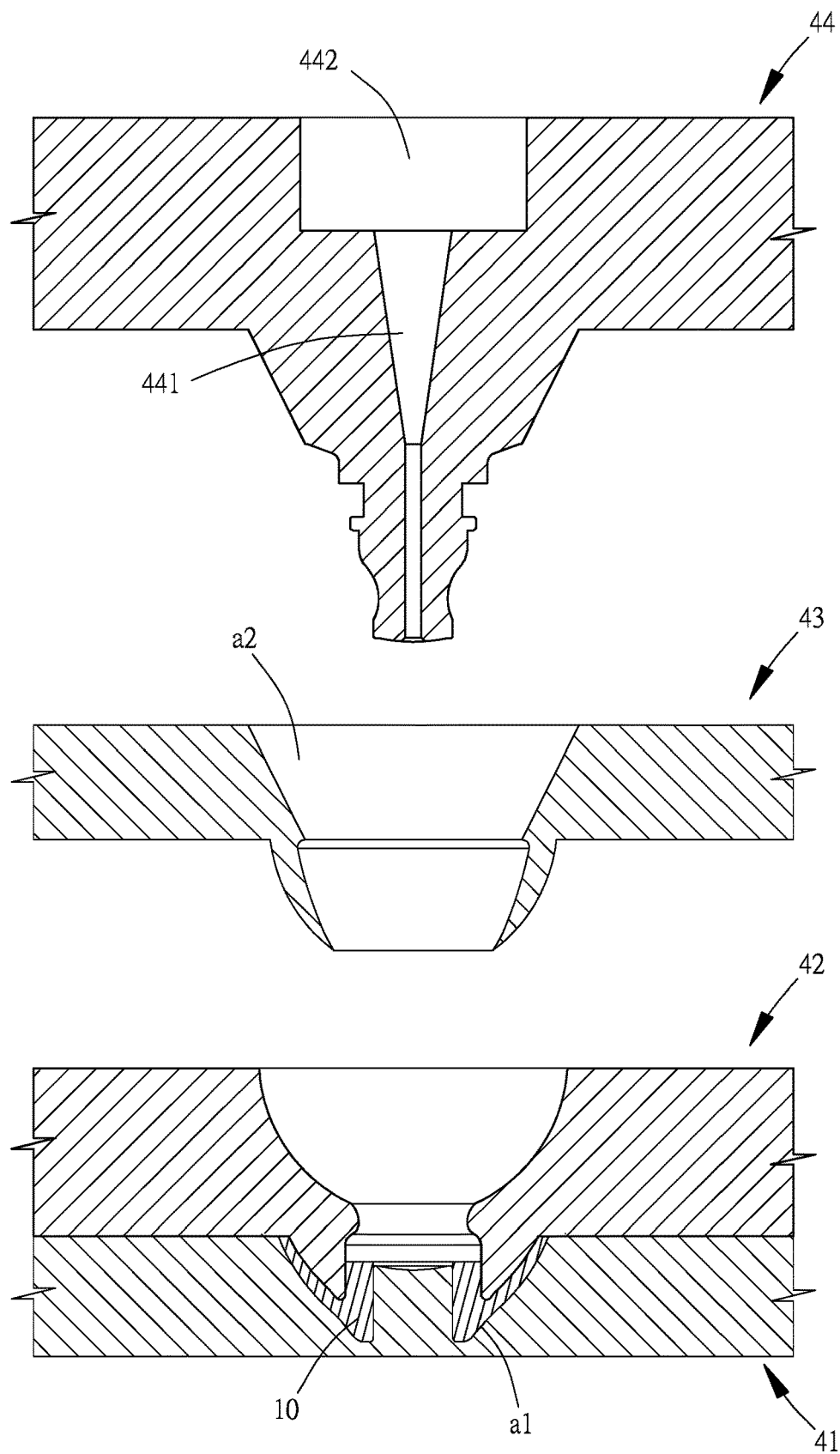
Figure 7C:
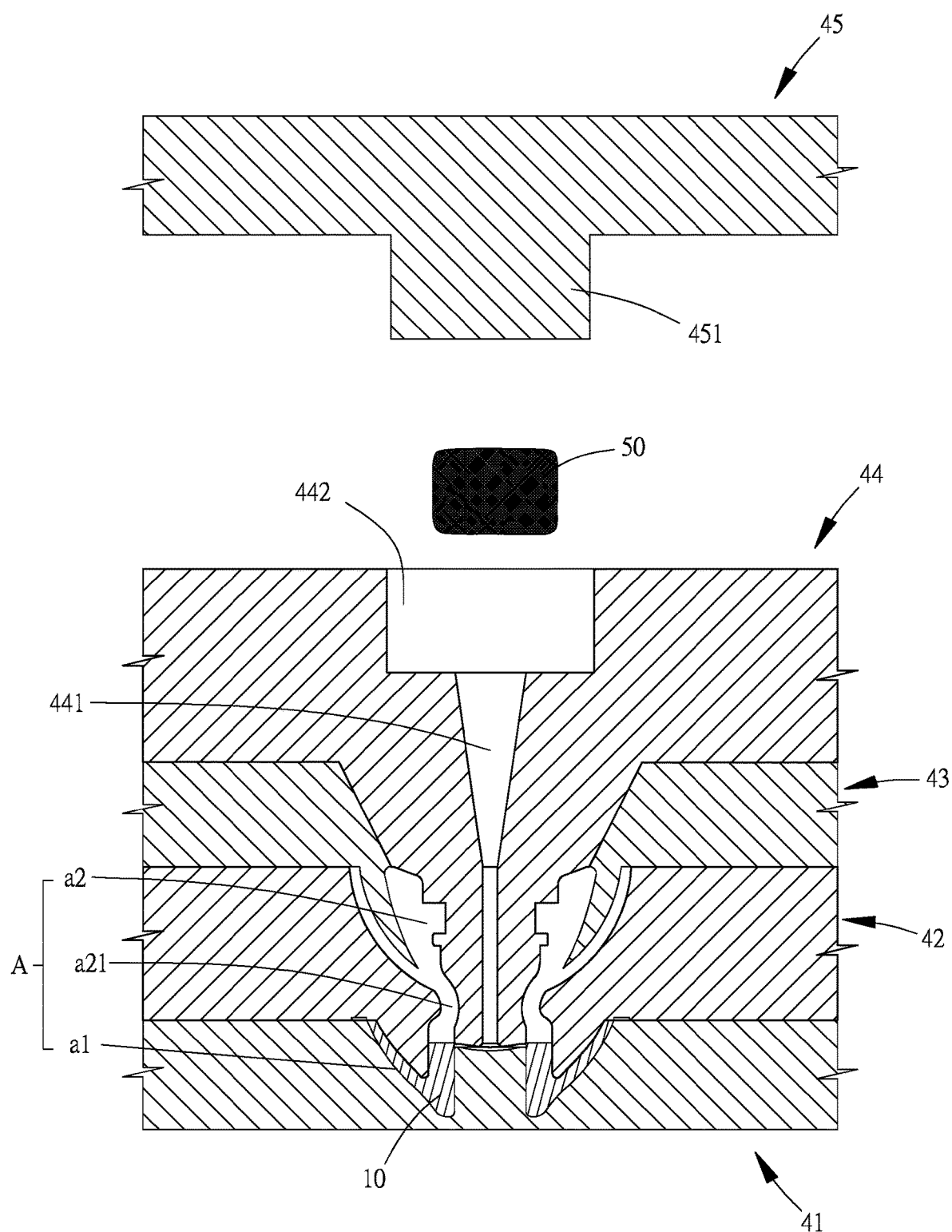

The aforesaid mold device is applicable to a method of manufacturing an eartip. Referring to FIG. 5, there is shown a schematic view of the process flow of the method of manufacturing an eartip according to the present invention. The method comprises steps as follows:

Step 1: placing an upper bevel portion raw material in a first mold unit 30: placing an upper bevel portion raw material 50, that is, silicone of a rigidity of around 30±5, in the recess 321 (as shown in FIG. 6A) formed at the lower mold 32 of the first mold unit 30;

Step 2: forming an upper bevel portion: stacking and squeezing the upper mold 31 and the lower mold 32 of the first mold unit 30 to introduce the upper bevel portion raw material 50 into the upper bevel cavity 33 between the upper mold 31 and the lower mold 32, so as to form an upper bevel portion 10 having a hollow-cored guiding tube 11 and an upper bevel 12 (as shown in FIG. 6B);

Step 3: releasing the first mold unit: separating the upper mold 31 and the lower mold 32 (as shown in FIG. 6C);

Step 4: removing the upper bevel portion: removing the upper bevel portion 10 otherwise attached to the upper mold 31 or the lower mold 32 (as shown in FIG. 6D);

Step 5: placing the upper bevel portion in the second mold unit: placing the upper bevel portion 10 in the upper bevel receiving cavity a1 between a first mold 41 and a second mold 42 of a second mold unit 40 (as shown in FIGS. 7A and 7B);

Step 6: assembling the second mold unit to form a lower bevel cavity: putting together the second mold 42, third mold 43, and fourth mold 44 in sequence to form a lower bevel cavity a2 and form at the bottom of the lower bevel cavity a2 an annular buffer cavity a21 which curves inward (as shown in FIG. 7C);

Step 7: placing a lower bevel portion raw material in the second mold unit: placing a lower bevel portion raw material

Figure 7D:
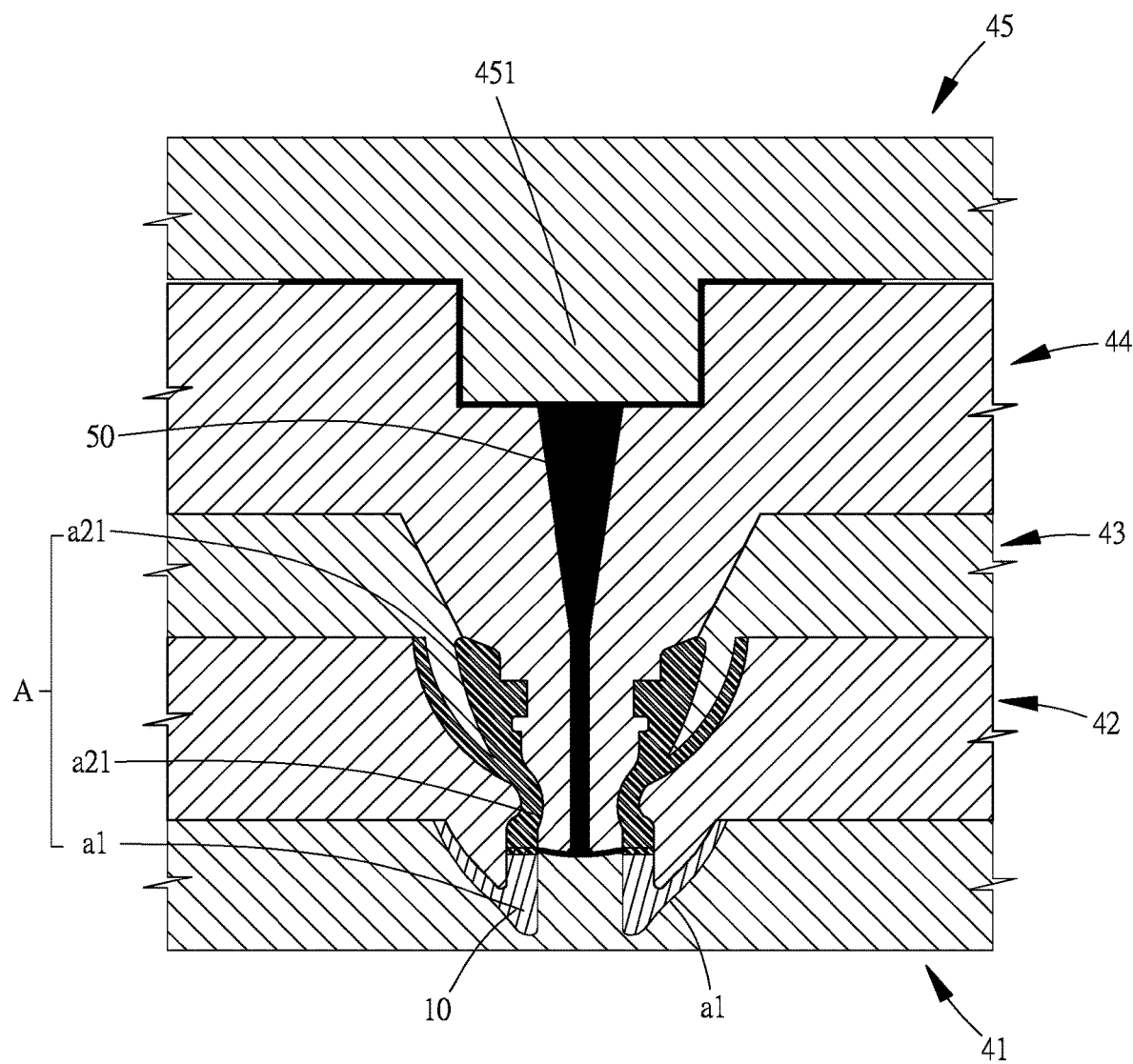
Figure 7E:
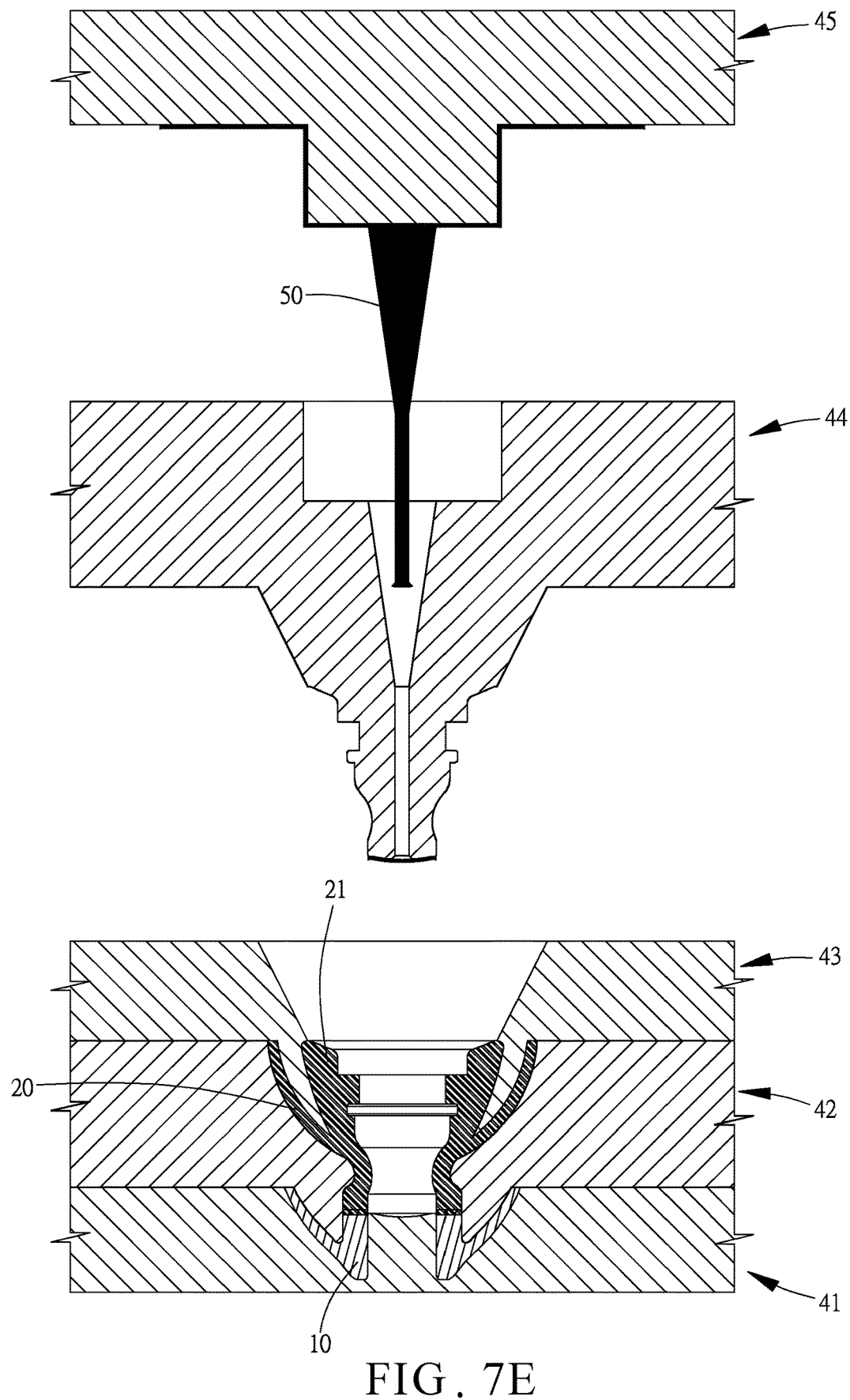
Figure 7F:
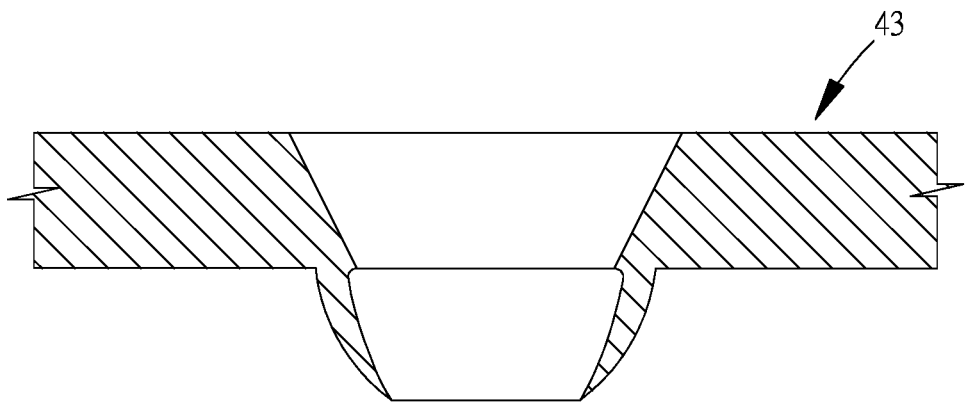
Figure 7F:
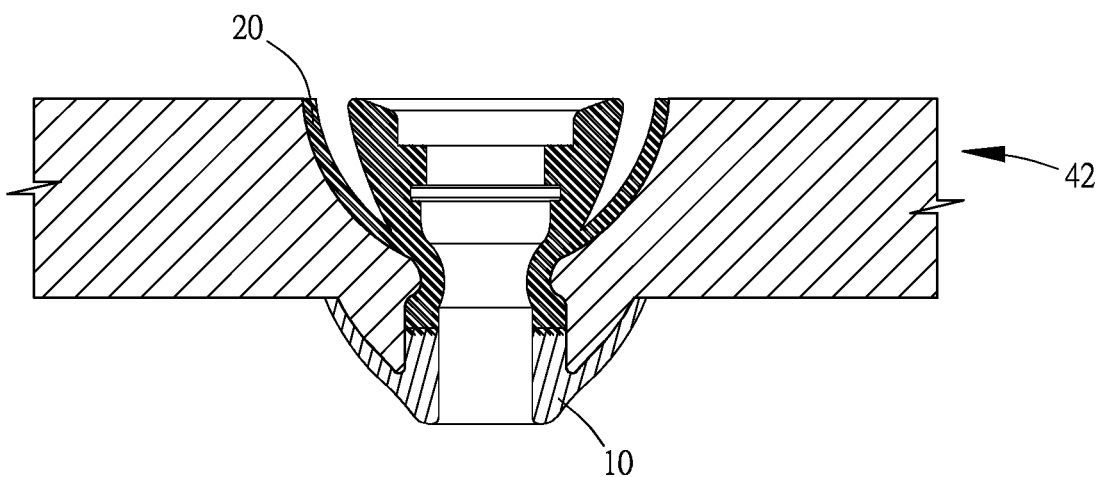
Figure 7F:
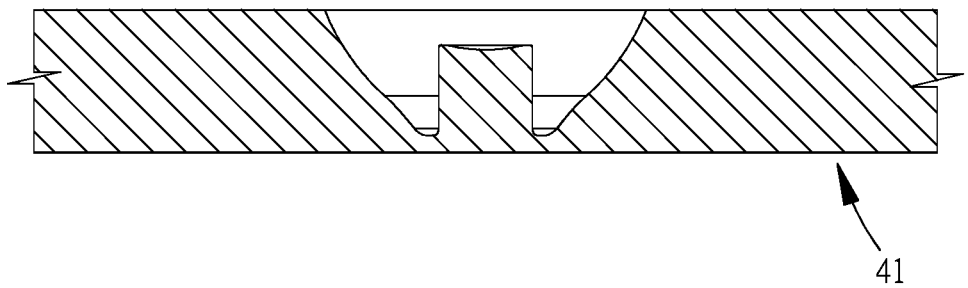
Figure 8:
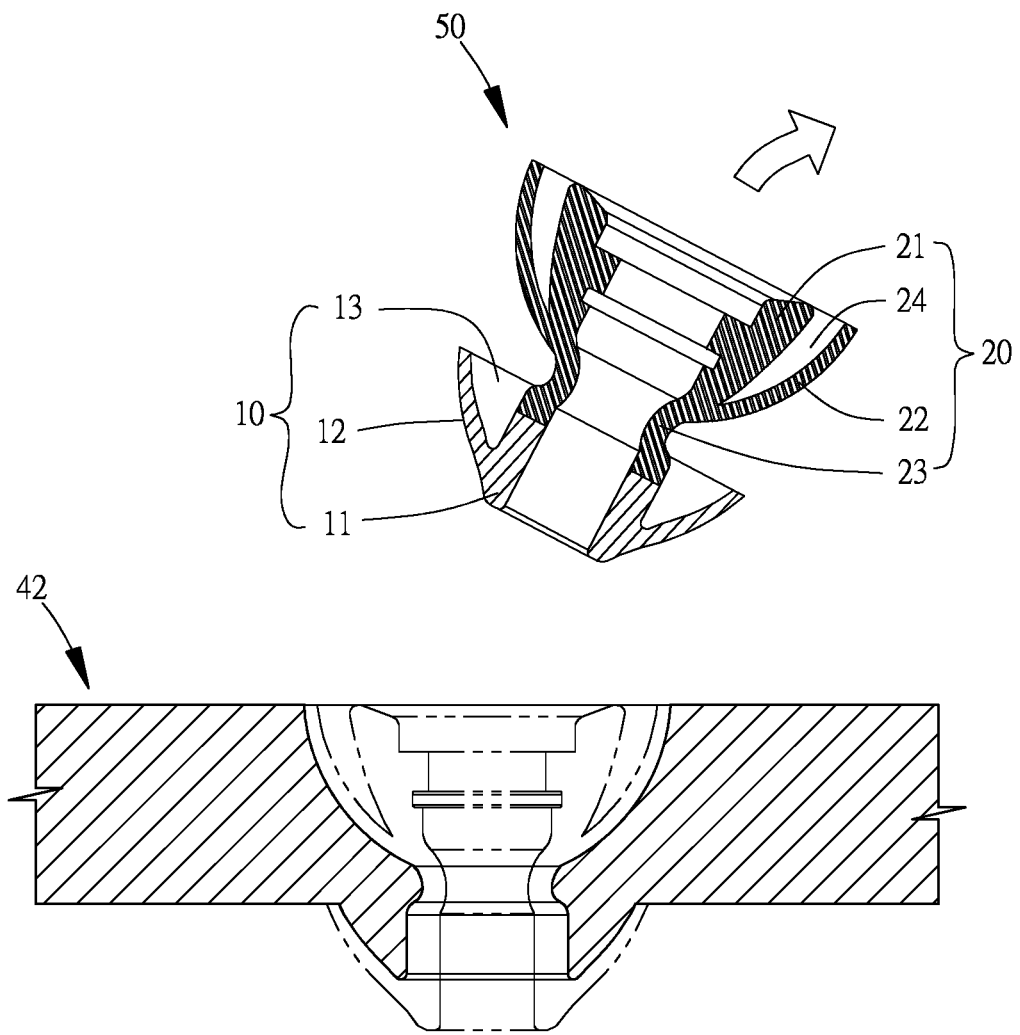
FIG. 8 is a schematic view of how to remove the eartip at the end of the manufacturing process.

60, that is, silicone of a rigidity of around 40±5, in the raw material storage chamber 442 of the fourth mold 44 (as shown in FIG. 7C);

Step 8: forming a lower bevel portion: fitting the fifth mold inside the fourth mold 44 so that not only is the lower bevel portion raw material 60 introduced from the raw material storage chamber 442 into the lower bevel cavity a2 through the hollow-cored raw material guiding pipe 441 to therefore form a lower bevel portion 20, but the upper bevel portion 10 and the lower bevel portion 20 also join each other to form an eartip (as shown in FIG. 7D); and Step 9: performing mold release to remove an eartip: separating the first mold 41, the third mold 43, and the fourth mold 44 in a reverse order (as shown in FIGS. 7E, 7F), and then removing the eartip from the second mold 42 (as shown in FIG. 8).

The aforesaid steps, which involve placing silicone of a rigidity of around 30±5 in the first mold unit to form the upper bevel portion, placing the upper bevel portion in the upper bevel receiving cavity of the second mold unit, placing silicone of a rigidity of around 40±5 in the raw material storage chamber of the fourth mold, fitting the fifth mold inside the fourth mold so as to introduce silicone therefrom into the lower bevel cavity, thereby forming a lower bevel portion and allowing the upper bevel portion and the lower bevel portion to join each other to form an eartip, achieve advantages as follows: the silicone which the upper bevel portion is made of has a rigidity of around 30±5, and in consequence the upper bevel portion thus made is soft enough to reach the ear canal deeply; silicone which the lower bevel portion is made of has a rigidity of around 40±5, and in consequence the lower bevel portion thus made is rigid enough to close the ear canal; an annular buffer cavity which curves inward is formed at the bottom of the lower bevel cavity, and thus a buffer portion with a rigidity of around 40±5 is formed on top of the lower bevel portion to enable the upper bevel portion to bend when reaching the ear canal deeply, whereas the buffer portion is of an appropriate rigidity and thus does not bend readily, thereby allowing the upper bevel portion to reach the ear canal deeply.

The description of the embodiment indicates that the method of manufacturing an eartip according to the present invention entails using two molds and separating them in order to manufacture the eartip, wherein the eartip includes the upper and lower bevel portions made of raw materials which differ in rigidity, and in consequence the eartip thus manufactured and inserted into the ear canal is comfortable and unlikely to detach from the ear canal.

Although the present invention is disclosed above by preferred embodiments, the preferred embodiments are not restrictive of the present invention. Equivalent changes made by persons skilled in the art to the preferred embodiments, or equivalent implementation of the preferred embodiments, without departing from the spirit of the present invention must be deemed falling within the scope of the present invention.

What is claimed is:

1. An eartip, comprising:
    an upper bevel portion having an upper hollow-cored guiding tube and an upper bevel surrounding a top end of the upper hollow-cored guiding tube; and
    a lower bevel portion having a lower hollow-cored guiding tube and a lower bevel surrounding a top end of the lower hollow-cored guiding tube, wherein the top end of the lower hollow-cored guiding tube extends to form a buffer portion for connecting and communicating with the upper hollow-cored guiding tube, wherein a diameter of a bottom rim of the upper bevel is less than a diameter of a bottom rim of the lower bevel,
wherein
    the lower bevel portion is of a rigidity higher than a rigidity of the upper bevel portion, and wherein the buffer portion begins below a bottom edge of the upper bevel.

2. The eartip of claim 1, wherein the buffer portion is an annular groove.

3. The eartip of claim 2, wherein a space is disposed between the upper bevel and the upper hollow-cored guiding tube, and a space is disposed between the lower bevel and the lower hollow-cored guiding tube.

4. The eartip of claim 3, wherein the rigidity of the upper bevel portion is around 75% of the rigidity of the lower bevel portion.

5. The eartip of claim 4, wherein the upper bevel portion is made of a silicone-containing material.

6. The eartip of claim 1, wherein the rigidity of the lower bevel portion is around 25% higher than the rigidity of the upper bevel portion.

7. The eartip of claim 6, wherein the lower bevel portion is made of a silicone-containing material.

8. The eartip of claim 1, wherein
    the upper hollow-cored guiding tube extends uniformly at a first width from an upper opening of the upper hollow-cored guiding tube until reaching the buffer portion, and
    the buffer portion
        has a same width as the first width of the upper hollow-cored guiding tube at a point where the buffer portion joins the upper hollow-cored guiding tube and immediately narrows after the point where the buffer portion joins the upper hollow-cored guiding tube,
        narrows gradually to a second width, and
        widens gradually from the second width to a third width greater than the first width.

9. The eartip of claim 1, wherein the buffer portion has a same rigidity as a rigidity of the lower bevel portion.

10. The eartip of claim 8, wherein in a cross-sectional view an outer surface of the lower hollow-cored guiding tube slopes gradually outward below the buffer portion.

11. The eartip of claim 10, wherein in a cross-sectional view a shape of the outer surface of the lower hollow-cored guiding tube conforms to a shape of an inner surface of the lower bevel.

* * * * *